United States Patent [19]

Galazaka

[11] Patent Number: 5,178,619
[45] Date of Patent: Jan. 12, 1993

[54] ELECTROCAUTERY INSTRUMENT HAVING CORD WIND-UP DEVICE

[76] Inventor: Edmund G. Galazaka, 5895 Bennington Rd., Vernon, Mich. 48476

[21] Appl. No.: 706,311

[22] Filed: May 28, 1991

[51] Int. Cl.⁵ .............................................. A61B 17/39
[52] U.S. Cl. .................................. 606/41; 606/42; 242/107.6; 242/107.7
[58] Field of Search ..................... 606/34, 41, 42, 45, 606/49; 242/107.6, 107.7; 191/12.2 R, 12.4

[56] References Cited

U.S. PATENT DOCUMENTS

| | | | |
|---|---|---|---|
| 2,586,386 | 2/1952 | Ryan | 242/107.6 |
| 3,715,526 | 2/1973 | Blanch et al. | 191/12.2 |
| 4,112,950 | 9/1978 | Pike | 128/303.14 |
| 4,114,736 | 9/1978 | Scherenberg | 191/12.4 |
| 4,463,759 | 8/1984 | Garito et al. | 128/303.14 |
| 5,074,863 | 12/1991 | Dines | 606/41 |

FOREIGN PATENT DOCUMENTS

| | | | |
|---|---|---|---|
| 117159 | 7/1918 | United Kingdom | 242/107.6 |
| 652554 | 4/1951 | United Kingdom | 242/107.6 |

*Primary Examiner*—Lee S. Cohen
*Attorney, Agent, or Firm*—Charles W. Chandler

[57] ABSTRACT

An electrocautery device having an electrical conductor cord mounted on a reel to be secured to the operating room sterile drapes. The surgeon withdraws the device toward the operating area. The reel locks at the position of withdrawal when tension on the cord is released. The operating room personnel presses a rewind button to activate a rewind mechanism to wind the cord on the reel.

11 Claims, 2 Drawing Sheets

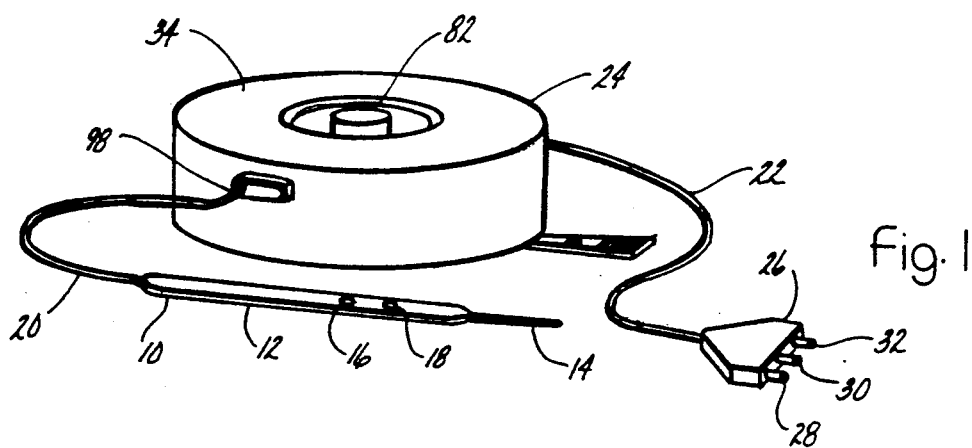
Fig. 1
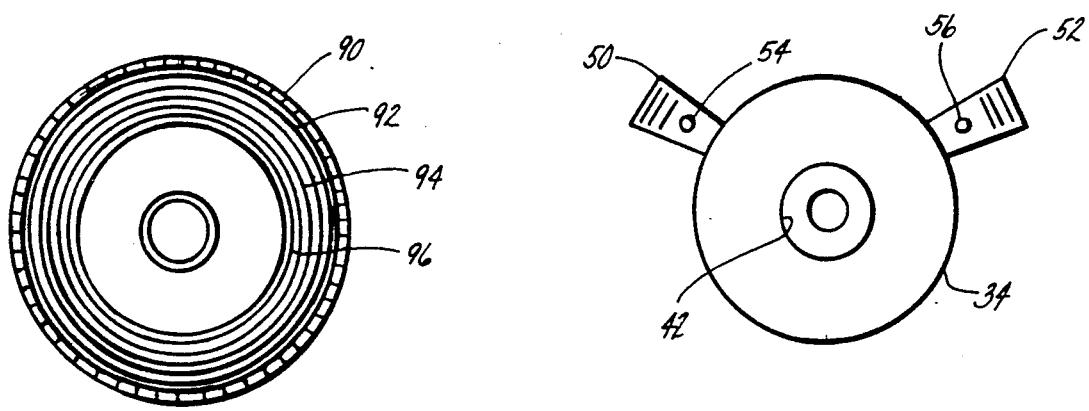
Fig. 4
Fig. 2
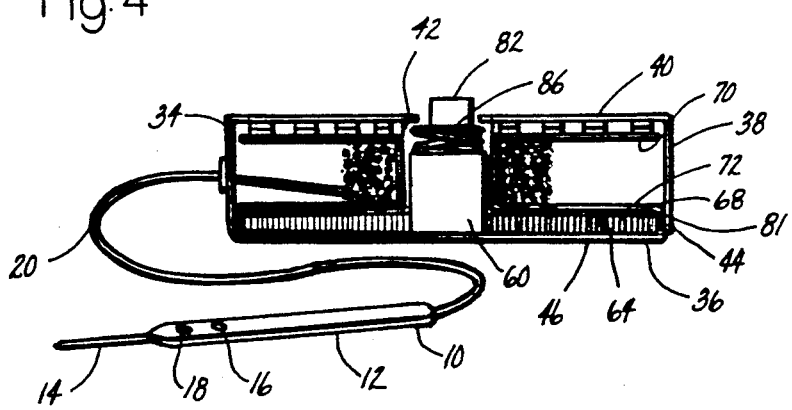
Fig. 3

1

ELECTROCAUTERY INSTRUMENT HAVING CORD WIND-UP DEVICE

BACKGROUND OF THE INVENTION

This invention is related to the field of electrosurgical instruments, and in particular, to a wind-up device for storing the cord of an electrocautery hand instrument.

A number of medical electronic instruments exist in the market for use by surgeons for diagnosis and treatment. An electrocautery instrument has a hand piece with a small metal probe. A finger-operated switch functions to deliver current to the probe. The energized probe contacts the patient to provide either a cutting function or a coagulation function depending upon which switch is being manipulated on the hand piece.

The hand piece has a long electrical cord connected to a power panel.

The problem is that the cord tends to become tangled with other instruments in the surgical operating area. The instrument is sterilized so that if it should be pulled off the operating area, it must be replaced. This is a relatively expensive procedure.

A typical electrocautery unit is shown in U.S. Pat. No. 4,112,950 which issued Sep. 12, 1978 to Harold L. Pike. Another unit is illustrated in U.S. Pat. No. 4,463,759, issued Aug. 7, 1984, to Jon C. Garito, Alan Ellman and Zvi Rozensher.

A miniaturized cord and reel is disclosed in U.S. Pat. No. 3,715,526 which issued Feb. 6, 1973 to Charles H. Blanch and James W. Kovacik.

U.S. Pat. No. 4,114,736, which issued Sep. 19, 1970 to Volker Scherenberg, shows a retractor for retracting a cord an electrical appliance.

SUMMARY OF THE INVENTION

The broad purpose of the present invention is to provide an electrocautery instrument having a conductor cord connected to a wind-up reel. The reel stores the cord into a housing until such time as the cautery hand set is to be used. Operating room personnel attach the reel housing to the sterile drapes. The surgeon withdraws the hand set toward the operating field. As the reel is unwound, a ratchet mechanism prevents the reel from being rewound until the user presses a rewind button. The spring-biased reel then rewinds the cord into the housing.

The reel housing has a rotary switch such that the hand piece can be electrically energized regardless of the amount of cord withdrawn from the reel.

Still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views and in which:

FIG. 1 illustrates an electrocautery device having a wind-up reel illustrating the preferred embodiment of the invention.

FIG. 2 is a plan view Of the reel housing.

FIG. 3 is a sectional view of the reel housing.

FIG. 4 is a view of the annular switch elements as seen along lines 4—4 of FIG. 5.

DESCRIPTION OF THE PREFERRED EMBODIMENT

Figure 5:
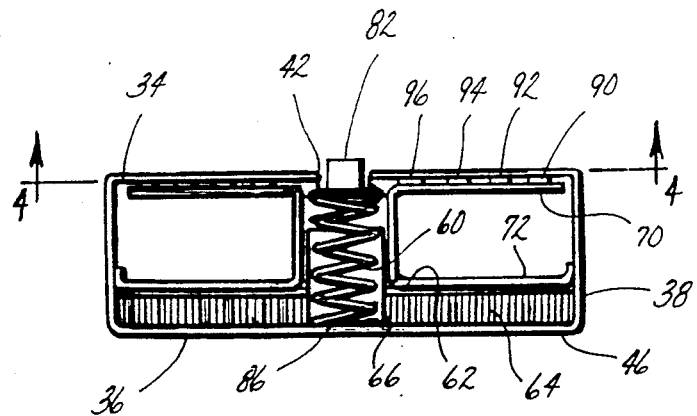
FIG. 5 is a sectional view similar to FIG. 3 but with the cord removed.

Referring to the drawings, a conventional, commercially available electrocautery handpiece 10 has an elongated casing 12 formed of a rigid plastic. A probe 14 of an electric conductive material extends from one end of casing 12. Push buttons 16 and 18 are operative to deliver an electrical current to the probe for either cutting or coagulating the patent's tissue, depending upon whether push button 16 or 18 is depressed.

A cord 20 having three internal electrical conductors (not shown) is connected to the rear end of the casing to form an electrical path with probe 14 when either button 16 or 18 is depressed. Cord 20 is connected by switch means, which will be described in greater detail, to a second cord 22 which extends from reel housing 24. Plug 26 has three prongs 28, 30, and 32 suited for connecting cord 20 to ground, a cutting current and a coagulation current, respectively. The plug is inserted into a conventional floor-mounted, electrical current source (not shown), when the hand piece is being used.

Referring to FIGS. 2 and 3, the reel housing comprises an upper housing 34 and a lower housing 36. Both housings are formed of a suitable plastic. The upper housing has a cylindrical side wall 38 and a flat top wall 40. Top wall 40 has a central opening 42.

The lower housing has a cylindrical side wall 44 and a planar bottom 46. The lower housing is telescopically received within the upper housing. The two side walls are attached together by a suitable adhesive, or in the alternative, by some sort of snap arrangement.

The lower housing has tabs 50 and 52. Tab 50 has an aperture 54, and tab 52 has an aperture 56. The tabs are located about 120 degrees apart with respect to the central axis of the housing. The two tabs are used for attaching the reel housing to the operating room sterile drapes.

Figure 6:
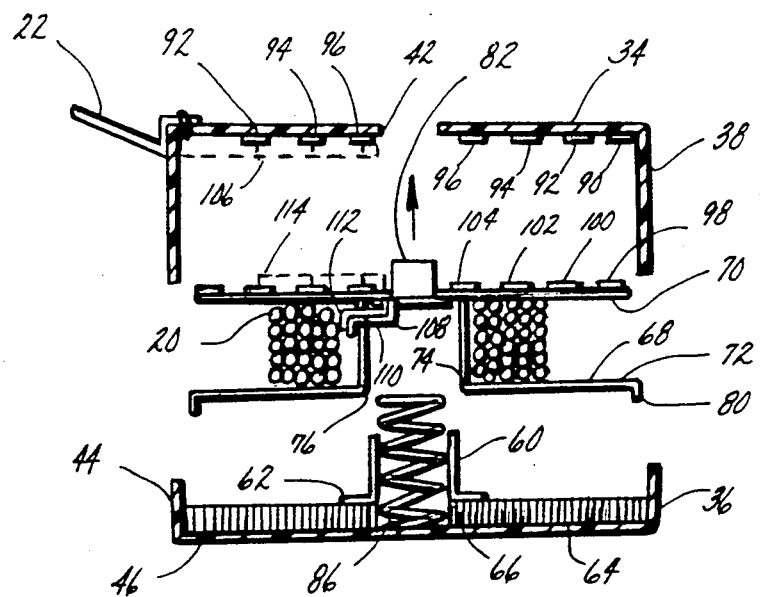
FIG. 6 is a partially exploded view of the reel housing.

Referring to FIG. 6, a cylindrical hub 60 is mounted in a central position on the bottom of the lower housing. The hub has an annular shoulder 62 spaced above bottom 46. A steel coil wind-up spring 64 is mounted on the bottom of the lower housing, beneath shoulder 62. The inner end 66 of the wind-up spring is attached to hub 60.

Reel 68 is mounted in the housing, and is also formed of a suitable plastic material. Reel 68 has a pair of circular plates 70 and 72 attached to a central cylindrical hub 74. The cord is wound around hub 74. Lower plate 72 has a central opening 76 so that hub 74 telescopically receives the upper end of hub 60 to a position in which plate 72 is seated on shoulder 62.

Referring to FIGS. 3 and 6, the lower reel plate has an annular skirt 80 which receives and contains the upper portion of wind-up spring 64. Spring 64 is attached at 81 to the skirt. The arrangement is such that the spring is wound up as the reel is rotated in the unwinding direction. When the reel is released, the wind-up spring biases the reel in the wind-up direction.

Referring to FIG. 5, push button 82 is attached to upper reel plate 70. The push button is received through opening 42 in the upper housing.

A helical compression spring 86 is disposed between the reel and the lower housing. The lower end of spring 86 is housed within hub 60 and seated on the bottom of the lower housing. The upper end of the spring is disposed in reel hub 74 and engages reel plate 70, beneath push button 82. Spring 86 urges the reel toward the top wall 40 of the upper housing. The user can separate the reel from top wall 40 by depressing button 82 against the bias of spring 86.

Figure 7:
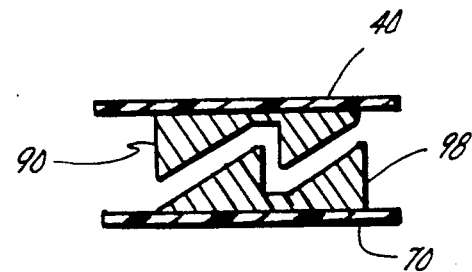
FIG. 7 is an enlarged fragmentary view of the ratchet mechanism.

Referring to FIGS. 4 and 5, concentric annular members 90, 92, 94 and 96 are mounted on the under surface of housing top wall 40. Annular ratchet member 90, the outermost ring, is a toothed member, illustrated in an enlarged manner, in FIG. 7. A companion annular ratchet member 98 is mounted on reel wall 70. The two ratchet members mate when the reel is closely adjacent the housing top wall. The ratchet teeth are complementary. When the reel engages the top wall the ratchet members permit reel rotation in the unwinding direction as cord 20 is pulled from the housing through opening 98. When the cord tension is relaxed, the ratchet teeth engage to lock the reel in position.

When the user depresses push button 82, the reel is pushed toward its seated position on shoulder 62. The two ratchet members are then separated sufficiently that the reel can be rotated in the wind-up direction under the influence of spring 64. When the reel is fully wound, only 4-6 inches of the cord extend from the housing.

Referring to FIG. 6, concentric spaced, raised, annular switch members 92, 94 and 96 are supported about the axis of rotation of the reel. Switch members 92, 94 and 96 are concentric circles of copper foil. The electrical contacts on the reel comprise three concentric copper foil rings 100, 102 and 104 which are opposed to switch members 92, 94 and 96, respectively. The switch members on the reel are raised sufficiently to engage their companion rings on the housing when the ratchet members are fully engaged.

Prongs 28 30 and 32 of plug 26 are internally connected by electrical conduit 106 to annular switch members 92, 94 and 96, respectively. The inner end of cord 20 has three electrical conductors 108, 110 and 112 internally connected by electrical conductor means 114 to rings 100, 102 and 104, respectively. Each pair of slidably engaged companion switch members form an electrical path from pins 28, 30 and 32 of plug 26 to hand piece 10. The electrical mode at the probe is governed by 16 and 18.

I have descried an automatic reel or a disposable electrocautery unit. The reel permits the surgeon to pull out the desired length of cord from the reel housing. The ratchet mechanism then prevents the reel from being rewound When the operating room personnel depresses button 82, the electrical contacts in the reel housing are broken, and the ratchet members are separated. The reel then winds the cord into the housing under the influence of coil spring 64.

The unit is relatively simple, easy to manufacture, reliable and can be formed of inexpensive materials in a disposable mode.

Having described my invention, I claim:

1. A medical apparatus for applying an electric current to a patient comprising:
   an electrocautery device having a handpiece and a conductive probe for applying current to the patient, an actuator button means movably mounted on the handpiece to be selectively operated by the user according to the desired current to be applied to the patient;
   a support;
   a reel rotatably mounted on the support about an axis of rotation for rotation either in an unwinding direction, or in the opposite wind-up direction;
   first bias means connected between the support and the reel for biasing the reel in the wind-up direction;
   the reel being moveable along said axis of rotation between a first position and a second position;
   locking means on the support operative to engage the reel to prevent rotation thereof in a wind-up direction, and to permit rotation of the reel in the wind-up direction when the reel is in the second position;
   a flexible, multiple conductor cord wound on the reel and being electrically connected to the handpiece to form part of an electrical path to the probe; and
   switch means mounted between the reel and the support for connecting the conductor cord to a source of electrical current, whereby the conductive probe is operative to apply the current to the patient.

2. A medical apparatus as defined in claim 1, in which the cord has three mutually-spaced, electrical conductors connected to said switch means.

3. A medical apparatus as defined in claim 1, in which the support comprises a housing, the reel being mounted in the housing.

4. A medical apparatus as defined in claim 1, in which the switch means comprises a first ring of electrically-conductive material mounted on the reel, and a second ring of electrically-conductive material mounted on the support in an opposed relationship to the first ring, on the support for moving the first and second rings either toward one another to make an electrical path therebetween, or away from one another to break said electrical path.

5. A medical apparatus as defined in claim 4, in which the rings are both mounted about the axis of rotation of the reel so as to form an electrical path therebetween in any rotated position of the reel with respect to the support.

6. A medical apparatus as defined in claim 4, said locking means including a bias member urging the reel toward the support to cause the rings to engage one another, and a push button means mounted on the reel for moving the reel away from the support to electrically separate the rings.

7. A medical apparatus as defined in claim 1, including a housing, said first bias means including a bias member mounted in the housing and engaged with the reel for urging it toward rotation in the wind-up direction for winding the cord about the reel.

8. A medical apparatus as defined in claim 1, said locking means including a first annular ratchet member having a continuous array of ratchet teeth, a second annular ratchet member having a continuous array of ratchet teeth that are complementary with the teeth of the first ratchet member, the second ratchet member being mounted on the support in an opposed relationship to the first ratchet member, on the support for moving the first and second ratchet members toward one another to lock the reel against rotation in the wind-up direction, or, away from one another to separate the ratchet members and permit the reel to rotate in the unwinding direction.

9. A medical apparatus as defined in claim 8, in which the ratchet members are both mounted about the axis of rotation of the reel so as to be operable to lock the reel against rotation in the wind-up direction.

10. A medical apparatus as defined in claim 8, including a bias member urging the reel toward the support to cause the ratchet members to engage one another, and push button means for moving the reel away from the support to separate the ratchet members.

11. An electrocautery apparatus for applying an electric current to a patient, comprising:
- a slender, elongated casing of a rigid plastic with axial openings at opposite ends thereof, the casing having first and second actuator buttons;
- a conductive probe received in the opening in one of said casing ends;
- a multiple conductor flexible cord having at least first and second electrical conductors received in the opposite end of the casing;
- a housing;
- a reel member mounted in the housing for rotation about an axis of rotation so as to be rotatable in either a wind-up direction or in the opposite, unwinding direction;
- a first bias member in the housing biasing the reel member in the wind-up direction;
- the cord being wound on the reel member, one end of the cord being received at the opposite end of the casing such that electrical current to the conductive probe may be controlled by manipulating the first and second actuator buttons;
- first switch means and second switch means for connecting the cord to a source of electrical current, the first switch means including a plurality of spaced, annular first conductor elements;
- the second switch means comprising a plurality of annular second conductor elements, each of the first conductor elements being associated with one of said second conductor elements;
- one of the switch means being mounted on the housing, the other of the switch means being mounted on the reel member such that the first conductor elements are each slideably engageable with the second conductor elements in any rotated position of the reel member with respect to the housing, to form an electrical path therebetween;
- the reel member being moveable along said axis of rotation between first and second spaced ratchet positions;
- a second bias member in the housing biasing the reel toward the first ratchet position, and a push button mounted on the reel for urging the reel toward said second ratchet position;
- ratchet means mounted between the reel and the housing, operative to restrain rotation of the reel in the wind-up direction when the reel is in said first position; and
- the cord being electrically connected to the switch means mounted on the reel member, and means for connecting the other switch means to a source of electrical current.

* * * * *

UNITED STATES PATENT AND TRADEMARK OFFICE
CERTIFICATE OF CORRECTION

PATENT NO. : 5,178,619

DATED : January 12, 1993

INVENTOR(S) : Edmund G. Galazka

It is certified that error appears in the above-identified patent and that said Letters Patent is hereby corrected as shown below:

On the title page, Item [76], Inventor Edmund G. Galazaka should read --Edmund G. Galazka--.

Signed and Sealed this

Twenty-first Day of December, 1993

Attest:

BRUCE LEHMAN

Attesting Officer

Commissioner of Patents and Trademarks